United States Patent [19]

Homeier

[11] 4,070,403

[45] Jan. 24, 1978

[54] CATALYTIC HYDROFORMYLATION PROCESS

[75] Inventor: Edwin H. Homeier, Maywood, Ill.

[73] Assignee: UOP Inc., Des Plaines, Ill.

[21] Appl. No.: 767,274

[22] Filed: Feb. 10, 1977

Related U.S. Application Data

[63] Continuation-in-part of Ser. No. 597,725, July 21, 1975, abandoned, which is a continuation-in-part of Ser. No. 491,705, July 25, 1974, abandoned.

[51] Int. Cl.$^2$ .............................................. C07C 27/22
[52] U.S. Cl. ............................. 260/632 HF; 252/459; 260/604 HF
[58] Field of Search .................. 260/632 HF, 604 HF

[56] References Cited

U.S. PATENT DOCUMENTS

| | | | |
|---|---|---|---|
| 3,013,990 | 12/1961 | Breck et al. | 252/455 Z |
| 3,102,899 | 9/1963 | Cannell | 260/632 HF |
| 3,239,569 | 3/1966 | Slaugh et al. | 260/632 HF |
| 3,677,973 | 7/1972 | Mitsche et al. | 252/455 Z |
| 3,733,362 | 5/1973 | Bisle | 260/632 HF |
| 3,880,938 | 4/1975 | Massie | 260/632 HF |
| 3,989,759 | 11/1976 | Yoo | 260/604 HF |
| 3,991,119 | 11/1976 | Yoo | 260/604 HF |

*Primary Examiner*—Joseph E. Evans
*Attorney, Agent, or Firm*—James R. Hoatson, Jr.; Raymond H. Nelson; William H. Page, II

[57] ABSTRACT

The hydroformylation of olefinic hydrocarbons is effected by treating the hydrocarbon with hydrogen and carbon monoxide in the presence of a catalyst system which comprises a cobalt-containing compound chemically bonded to a zeolite-alumina hydrosol dispersion. The reaction is effected at temperatures ranging from about 70° to about 300° C. and pressures ranging from about 1 to about 500 atmospheres.

16 Claims, No Drawings

CATALYTIC HYDROFORMYLATION PROCESS

CROSS-REFERENCE TO RELATED APPLICATIONS

This application is a continuation-in-part of copending application Ser. No. 597,725 filed July 21, 1975 and now abandoned which is a continuation-in-part of copending application Ser No. 491,705 filed July 25, 1974 and now abandoned, all teachings of which are incorporated herein by reference thereto.

This invention relates to a hydroformylation process and specifically to a novel hydroformylation process for the preparation of alcohols and/or aldehydes. The process is effected by treating an olefinic hydrocarbon with hydrogen and carbon monoxide in the presence of a novel catalyst system comprising a cobalt-containing compound chemically bonded to a zeolite-alumina hydrosol dispersion.

Processes directed to the production of reaction mixtures comprising substantial amounts of aldehydes and alcohols by the hydroformylation of olefinic hydrocarbons with carbon monoxide and hydrogen in the presence of certain catalysts are well-known in the art. The aldehydes and alcohols produced generally correspond to the compounds obtained by the addition of a carbonyl or carbinol group to an olefinic hydrocarbon in the starting material with simultaneous saturation of the olefin bond. The process is known as hydroformylation and it involves a reaction which may be shown by the generic formula:

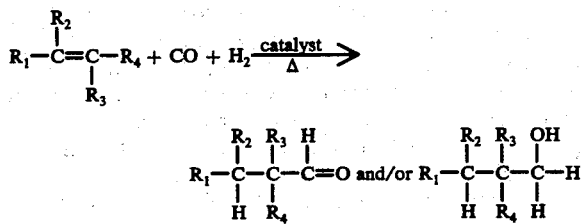

where $R_1$, $R_2$, $R_3$, or $R_4$ may be chosen from a group comprising an organic, halide or hydrogen radical.

It has been shown in the prior art that dicobalt octacarbonyl has generally been used as the catalyst for the hydroformylation of the olefinic hydrocarbons. This catalyst, which can be prepared from many forms of cobalt, usually decomposes rapidly at hydroformylation temperatures unless high pressures of about 200-4500 lbs. per sq. inch gauge of carbon monoxide are maintained.

The catalytic composition of matter of the present invention possesses two basic components: (1) a cobalt-containing compound and (2) a zeolite-alumina hydrosol dispersion. In U.S. Pat. No. 3,880,938 a process is disclosed for hydroformylating an unsaturated compound with carbon monoxide and hydrogen in the presence of a cobalt-containing compound and a zeolite-alumina hydrosol dispersion. The disadvantage of this type of process is the difficult catalyst recovery in homogeneous reaction systems. The unexpected aspect of this invention resides in the fact that the cobalt-containing compound may adequately be dispersed upon the surface of aluminated zeolite support and not detrimentally affect the resultant preparation of alcohols and/or aldehydes. The dispersal of any catalytic metal upon a support solid involves problems of reactant contact, surface area, adhesion of the catalytic element to the support surface, change in catalytic activity, reactant passage in the reaction zone, mixing of the reactants in vaporous phase etc. It has been unexpectedly found that these problems can be minimized by a vapor phase impregnation of the solid support and allow the manufacturer a novel heterogeneous catalyst system utilizing the two components set forth in U.S. Pat. No. 3,880,938. The advantage or utility of the heterogeneous catalyst system resides in that the catalyst metal may be easily separated from the reactants and products by physical removal of the zeolitic bed. The advantage can further be seen in a comparison of the physical and financial expenditures necessary to separate and purify the cobalt-containing compounds from a slurry containing alcohols and/or aldehydes, zeolitic material and unreacted olefinic hydrocarbons in comparison with the mere "lifting out" of the solid support of the heterogeneous solid support. In contradistinction to the prior art it has now been found that a cobalt-containing compound chemically bound to a zeolite material which has been dispersed in an alumina hydrosol prior to aging at an elevated temperature will effect the hydroformylation of an olefinic bond in a heterogeneous catalytic system.

The desired products of the process of this invention, namely, alcohols and aldehydes, are utilized in the chemical industry in many ways. For example, alcohols are utilized in the synthesizing of other organic derivatives, as solvents, as an extraction medium, in dyes, synthetic drugs, synthetic rubbers, detergents, cleaning solutions, surface coatings, cosmetics, pharmaceuticals, in the preparation of esters, as a solvent for resin in coatings, in plasticizers, dyeing assistants, hydraulic fluids, detergent formulations and dehydrating agents. Aldehydes are utilized as perfumeries or precursors to perfumeries, or in the synthesis of primary alcohols. The non-linear alcohols and aldehydes are also utilized in the chemical industry in many other ways; for example, 2-methyl-1-butanol is utilized as a solvent in varnishes, lacquers and paint removers. Likewise, a general use of the non-linear alcohols and aldehydes is in detergent formulations as exemplified by 2-butyl-1-heptanol.

It is therefore an object of this invention to provide a catalytic process for the preparation of aldehydes and alcohols.

A further object of this invention is to provide an improved heterogeneous catalyst system for the preparation of alcohols and aldehydes utilizing a cobalt-containing compound chemically bound to a zeolitealumina hydrosol dispersion in a more expedient and pecuniarily rewarding catalytic manner.

In one aspect an embodiment of this invention resides in a process for the hydroformylation of an olefinic hydrocarbon which comprises treating said hydrocarbon with carbon monoxide and hydrogen at hydroformylation conditions in the presence of a catalyst system comprising a cobalt-containing compound chemically bonded to a zeolite-alumina hydrosol dispersion which has been aged at a temperature of from about 30° to about 500° C. and recovering the resultant hydroformylated products.

A specific embodiment of this invention is found in a process for the hydroformylation of an olefinic hydrocarbon which comprises treating decene-5 with hydrogen and carbon monoxide at a temperature in the range of from about 75° to about 300° C. and a pressure in the range of from about 1 to about 500 atmospheres in the presence of a catalyst comprising 0.39 wt. % cobalt hydroiodocarbonyl dispersed on 99.61 wt. % alumina hydrosol-treated mordenite and recovering the resultant undecanols and undecanals.

Other objects and embodiments will be found in the following further detailed description of the present invention.

As hereinbefore set forth the present invention is concerned with a process for preparing alcohols and aldehydes from unsaturated compounds, the process being effected by the hydroformulation of an olefinic hydrocarbon with carbon monoxide and hydrogen in the presence of a catalyst system comprising a cobalt-containing compound chemically bound to a zeolite-alumina hydrosol dispersion. This catalyst system differs from the prior art as exemplified by the hereinbefore discussed U.S. Pat. No. 3,880,938. As hereinbefore discussed, this reference utilizes a catalyst such as dicobalt octacarbonyl coextensively with a hydrosol treated mordenite. This catalyst does not comprise a cobalt-containing compound which is chemically bound to the mordenite. The catalyst of the reference which is homogeneous in nature is distinct from the heterogeneous catalyst of the present invention. Likewise, other prior art patents such as U.S. Pat. Nos. 3,013,990 or 3,677,973 also disclose metallic catalytic components which are dispersed on supports such as aluminosilicate compounds. However, as in the case of U.S. Pat. No. 3,880,938 these catalyst composites are not chemically bound but rather are in the form of a metal dispersed on a support. By utilizing such a catalyst composite of the prior art certain disadvantages will be present inasmuch as a portion of the soluble metal will be lost during the process thereby necessitating a renewal of the catalyst composite in order to effectively convert the unsaturated compound to the desired alcohols or aldehydes and requiring expensive recovery of the soluble metal from the product solution. By utilizing the catalyst composite of the present invention in which the cobalt-containing compound is chemically bound to the zeolite-alumina sol dispersion, it is possible by utilizing such a heterogeneous catalyst system, to effect the hydroformylation of the unsaturated compound in such a manner so that there will be a minimal loss of catalyst and thus will enable the process to be effected in a more economical manner.

The hydroformylation of the unsaturated compound by treatment with carbon monoxide and hydrogen in the presence of the catalyst system of the present invention will be effected at hydroformylation conditions which include a temperature in the range of from bout 75° to about 300° C., and preferably in a range of from about 100° to about 200° C. In addition, the reaction is also effected under superatmospheric pressures ranging from 1 up to about 500 atmospheres or more. The superatmospheric pressures are afforded by the introduction of gaseous carbon monoxide and hydrogen to the reaction zone or, if so desired, the pressure may be partially afforded by the carbon monoxide or hydrogen while the remaining pressure in afforded by a substantially inert gas such as nitrogen, helium or carbon dioxide although not necessarily with equivalent results.

Examples of suitable olefinic hydrocarbons which are utilized as a starting material in the hydroformylation process of this invention include, in particular, propylene, butene-1, butene-2, isobutene, pentene-1, pentene-2, 2-methylbutene-1, 2-methylbutene-2, hexene-1, 3-methylpentene-1, 2-methylpentene-2, heptene-2, 2-methylhexene-2, 3-methylhexene-2, octene-1, octene-2, octene-3, heptene-1, nonene-1, decene-1, 3-methylheptene-1, 2-methylheptene-2, nonene-3, 3-methyloctene-2, decene-2, decene-5, decene-4, decene-3, 3,4-dimethyloctene-2, 4-ethyloctene-2, undecene-3, undecene-4, undecene-2, undecene-1, undecene-5, 4-methyldecene-2, 4,5-dimethylnonene-2, dodecene-1, dodecene-2, dodecene-3, dodecene-4, dodecene-5, tridecene-1, tridecene-2, tridecene-3, tetradecene-2, tetradecene-3, tetradecene-4, tetradecene-5, tetradecene-6, tetradecene-7, pentadecene-4, pentadecene-5, pentadecene-6, pentadecene-1, hexadecene-1, heptadecene-2, heptadecene-1, hexadecene-3, or mixtures of linear internal and terminal olefins such as internal olefins possessing carbon numbers between 11 and 14, 15 and 18, or 18 and 21, etc.

It is also contemplated within the scope of the process of the present invention that the hydroformylation may be effected in an inert organic medium as exemplified by n-pentane, n-hexane, n-heptane, n-octane, n-nonane, isooctane (2,2,4-trimethylpentane), cyclohexane, methylcyclohexane, benzene, toluene, m-xylene, mesitylene, etc.

It is understood that the aforementioned olefinic hydrocarbons and inert reaction mediums are only representative of the class of compounds which may be employed in the present hydroformylation invention and that the present invention is not necessarily limited thereto.

The catalytic composition of matter of the present invention contains the essence of the novelty of the present invention. The catalytic compound is chemically bound to the zeolite-alumina hydrosol dispersion which has been aged at a temperture of about 30° to about 500° C. The weight percentage of cobalt-containing compound upon the zeolite material will range from about 0.0001 weight percent to about 20.000 weight percent. The catalyst system will be present in the hydroformylation reaction in a weight percent of about 0.1 weight percent to about 20 weight percent of the cobalt-containing compound per weight of the olefinic hydrocarbon. The catalyst and its two basic components will hereinafter be discussed in further detail.

Zeolites are crystalline aluminosilicates comprising cages or cavities interconnected by smaller pores or channels of definite size range characteristic of each zeolitic variety. Since the dimensions of the pores and channels are such as to accept molecules of certain dimension while rejecting those of larger dimensions the materials have come to be known as molecular sieves and are utilized in many ways taking advantage of these properties.

The zeolites are generally described as a three-dimensional network of fundamental structural units consisting of silicon-centered $SiO_4$ and aluminum-centered $ALO_4$ tetrahedra interconnected by a mutual sharing of apical oxygen atoms to effect a chemical balance, each $ALO_4$ tetrahdera has a cation associated therewith, typically sodium. The $SiO_4$ and $ALO_4$ tetrahedra are arranged in a definite geometric pattern often visualized either in terms of chains, layers or polyhedra. The zeolites comprise well-defined intra-crystalline dimensions including intra-crystalline channels and pores whose narrowest cross-section has essentially a uniform diameter. The various zeolites may be classified according to the geometric pattern of their framework with its attendant pore size, and by the $SiO_2:Al_2O_3$ mole ratio of their compositions.

One type of zeolitic catalyst contemplated within the scope of this invention is mordenite. Mordenite is highly siliceous in nature and characterized by a $SiO_2:Al_2O_3$ mole ratio of from about 6 to about 12 as manufactured or found in its natural state. The mordenite crystal structure comprises four and five membered rings of $SiO_2$ and $ALO_4$ tetrahedra so arranged that the resulting crystal lattice comprises pores and channels running parallel along the crystal axis to give a tubular configuration. Mordenite is unique among zeolites since the channels or tubes do not intersect and access to the cages or cavities is in only one direction, thereby giving the zeolitic structure its two-dimension configuration.

Another type of zeolitic catalyst contemplated within the scope of this invention is faujasite. Faujasite is characterized by a $SiO_2:Al_2O_3$ ratio of about 2 to about 6 and by pore openings in the range of from about 6 to about 15 Angstroms. The fundamental structural units, $SiO_4$ and $ALO_4$ tetrahedra, are joined to form four-membered and six-membered rings and the rings are so arranged that the resulting structure resembles a truncated octahedron with the four-membered ring forming six sides or faces thereof and the six-membered ring forming the remaining eight sides or faces. The resulting truncated octahedra are interconnected at the hexagonal faces through a hexagonal prism formed by two of the six-membered rings of tetrahedra to form a crystal lattice comprising cavities or cages in open communication through channels, thereby giving the zeolitic structure its three-dimensional configuratin. Other natural zeolites which may be utilized include analcite, chabazite, heulandite, natrolite, stilbite and thomsonite. It is also contemplated within the scope of the process of this invention that synthetic zeolitic catalyst may also be utilized. The synthetic zeolites would include all those varieties ranging from gelatinous to porous or sandlike.

The above mentioned zeolite is treated by a dispersion in an alumina hydrosol prior to aging at elevated temperatures. The treatment is a two-step process: first where the zeolite is dispersed within an alumina hydrosol, and second when it is aged at elevated temperature in the range of about 45° to about 200° C. and preferably in the range of about 90° to about 160° C. for a period of time from 1 to 20 hours or more. An alumina hydrosol may be prepared from compounds such as aluminum chloride, aluminum bromide, aluminum sulfate, aluminum alcoholate, etc., the aluminum chloride being the most generally employed. Suitable examples of alumina hydrosols would include aluminum halide hydrosols, such as aluminum chloride sols, aluminum bromide sols, aluminumchlorosulfate hydrosol and aluminum hydrosol.

The catalytic composite of the present invention comprises not only the above set forth zeolitic treated material but also the catalytically active cobalt-containing compound chemically bound to the material. Suitable examples of cobalt-containing compounds may be exemplified, in particular, by cobalt chloride, cobalt fluoride, cobalt iodide, cobalt acetate, cobalt propionate, cobalt nitrate, dicobalt octacarbonyl, hydridocobalt carbonyl [somtimes nomenclated as $HCo(CO)_4$] or the cobalt-containing compound may be present in the form of an oxide. It is also contemplated within the scope of this invention that any phosphorouscontaining compound may also be present as a ligand within the cobaltcontaining compound. Suitable phosphorous-containing components of the catalysts will comprise a trialkyl phosphine in which each alkyl is a lower alkyl having from 1 to 10 carbon atoms such as a tertiary organo phosphine as trimethyl phosphine, triethyl phosphine, tri-n-butyl phosphine, triamyl phosphine, trihexyl phosphine, tripropyl phosphine, trinonyl phosphine, tridecyl phosphine, tri-n-butyloctadecyl phosphine, dimethylethyl phosphine, diamyl phosphine, ethyl-bis-(beta-phenylethyl)phosphine, tricyclopentyl phosphine, tricyclohexyl phosphine, dimethylpentyl phosphine, trioctyl phosphine, diphenylmethyl phosphine, diphenylbutyl phosphine, diphenylbenzyl phosphine, trifluorophosphine, diethylphenyl phosphine, etc.

The impregnation of the zeolitic material with the cobalt-containing compound may be performed by the preferred vapor phase dispersion of the catalytically active cobalt compound upon the alumina hydrosol treated zeolite as exemplified in Example I below. In one embodiment the catalysts may be prepared in situ in an appropriate reactor for a hydroformylation reaction whereby the aluminum-treated zeolitic material is impregnated with a catalytically active cobalt-containing compound or a precursor of the cobalt-containing compound within said hydroformylation reactor. In another embodiment a cobalt-containing compound and any respective phosphine ligands or compounds may also be chemically bound to the aluminum-treated zeolitic material prior to being placed in the hydroformylation reactor. It should be noted that the cobalt-containing compound chemically bonded to the zeolite-alumina hydrosol dispersion should be separated from any cobalt-containing compound which is not chemically bonded to the zeolite-alumina hydrosol dispersion by an appropriate washing procedure before the heterogeneous catalyst is used since dissolution of the cobalt compound which is not chemically bonded to said zeolite-alumina hydrosol dispersion will otherwise occur during the hydroformylation process leading or loss of cobalt to the product stream. The preferred appropriate washing procedure which will remove the cobalt not chemically bonded to the zeolite-alumina hydrosol dispersion comprises extraction of the cobalt which is not chemically bonded to the support by hydrocarbon under a carbon monoxide atmosphere. It is contemplated within the scope of this invention that other washing procedues may be used, although not necessarily with equivalent results. It should also be noted that the heterogeneous catalyst comprising the cobalt-containing compound chemically bonded to the zeolite-alumina hydrosol dispersion may be either activated in situ in the hydroformylation reactor or may be activated prior to charging to the hydroformylation zone.

The following examples are given to illustrate the novel catalytic composite and the method for preparing said composite and are not intended to limit the generally broad scope of the present invention in strict accordance therewith.

EXAMPLE I

In this example mordenite was treated in a 33% aluminum chloride- 67% aluminum sulfate hydrosol bath and agent for 6 hours at 80° C. prior to drying and calcining whereby 16.0 grams of aluminated mordenite containing 15% mordenite was recovered. The catalytic composite involved in the composition of the present invention was prepared by passing gaseous cobalt hydridocarbonyl (generated by adding a solution of pyridinium cobalt tetracarbonyl dropwise to concentrated sulfuric acid) in a carbon monoxide stream over the aluminated mordenite which was held in the thimble of a Soxhlet extractor. The gaseous cobalt hydridocarbonyl condensed on the catalyst support, namely the aluminated mordenite, turning the colorless aluminated mordenite spheres deep red. The spheres were exposed to about 8.8 mmoles (1.5 grams) of cobalt hydridocarbonyl over a period of several hours. The mixture was allowed to stand at room temperature in a carbon monoxide atmosphere over a period of time comprising 48 hours in order to facilitate the bonding of the cobalt to the acid alumina sites as shown in the following equation:

wherein ∫ denotes the aluminated mordenite. The excess carbonyl was removed by extraction of the impregnated spheres under a carbon monoxide atmosphere with pentane until the extraction liquid, which was initially red, became colorless to the eye, said time comprising approximately 5 hours. The spheres which were now blue were removed and stored in a carbon monoxide atmosphere for a period of time comprising 72 hours prior to use as set forth in Examples II, III, IV and V below. Chemical analysis of a sample of the spheres for cobalt disclosed that they contained 0.39 weight percent cobalt dispersed on the aluminated mordenite.

EXAMPLE II

In this example 10.0 grams of the above set forth catalyst composite was charged to a nitrogen flushed 850 milliliter glass-lined autoclave which contained 20.0 grams of decene-5. The liner was sealed in the autoclave and pressurized to 120 atmospheres of hydroen and 120 atmospheres of carbon monoxide. After heating to a temperature of 120° C. for a period of time comprising 18 hours the autoclave was allowed to return to room temperature and then the excess gas pressure was vented to the hood. The liquid product was recovered from the autoclave and analyzed by means of gas-liquid chromatography instrumentation, said analysis indicating a 2.1 weight percentage of undecanal, 88.7 weight percent of branched-chain undecanals, 0.5 weight percent of n-undecanol, 7.4 weight percent of branched-chained undecanols and 0.7 weight percent of decane. The recovered sphere were observed to be very dark blue when wet with the hydroformulation mixture and the blue color which persisted on standing for several weeks was seen to be distributed throughout the spheres.

Analysis of the organic product recovered from the experiment for cobalt disclosed that more than 92 weight percent of the heterogeneous cobalt originally charged to the reactor remained adsorbed on the aluminated mordenite at the conclusion of the reaction. This finding proves that a heterogeneous catalyst was formed. The same catalyst was reused in an identical hydroformylation reaction to determine the feasibility of catalyst reuse in hydroformylation reactions. Comparable conversions of the decene-5 were obtained utilizing the previously used cobalt-dispersed aluminated mordenite.

It should also be noted that the composition of the aldehydes and alcohols in this example (viz 98.8 weight percent) possessed a more desirable proportion of internal isomers (96.1 weight percent) than resulted from using the homogeneous dicobalt octacarbonyl catalyst. Thus, under identical reaction conditions except that homogeneous dicobalt octacarbonyl was used in place of the heterogeneous catalyst of the above described example only about 70 weight percent of the aldehydes and alcohols were internal isomers compared to the 96.1 weight percent of internal isomers achieved in this example.

EXAMPLE III

In this example experiments were performed to demonstrate the advantage of utilizing the novel heterogeneous catalyst of the present invention in a hydroformylation process. To prepare the catalyst in situ, 10 grams of aluminated mordenite spheres which were prepared according to the method set forth in Example I above along with 0.66 mmoles of dicobalt octacarbonyl and 143 mmoles of decene-5 were placed in a rotating autoclave. The autocalve was then sealed and 120 atmospheres each of carbon monoxide and hydrogen were charged thereto. The autoclave was rotated for a period of 18 hours at a temperature of 120° C. At the end of this 18-hour period, the autoclave was cooled and the excess gas was released.

The reaction mixture was removed from the autoclave and the solid catalyst was separated from the liquid by decantation. Following this, the catalyst was extracted with heptane under a carbon monoxide blanket to remove soluble cobalt complexes and to bond the cobalt to the alumina sites. The resultant light blue catalyst was analyzed for cobalt content, said analysis disclosing the presence of 0.38 mmoles of cobalt which was chemically bonded to the aluminated mordenite spheres. It is to be noted that there was a loss of 0.28 mmoles of dicobalt octacarbonyl during said extraction.

The resulting heterogeneous catalyst was recovered and charged to an 850 ml glass-lined, rotating stainless steel autoclave along with 171 mmoles of decene-5. Following a nitrogen flush of the autoclave, it was sealed and pressurized to 240 atmospheres utilizing 120 atmospheres each of carbon monoxide and hydrogen. The autoclave was then heated to a temperature of 160° C. and maintained thereat for a period of 36 hours. At the end of the 36-hour period, heating was discontinued, the autoclave was cooled, the excess pressure was vented to a hood and the products were removed from the autoclave. The heterogeneous catalyst comprising cobalt carbonyl chemically bonded to the aluminated mordenite spheres was separated from the organic products by decantation. A gasliquid chromatographic analysis of the liquid disclosed a 93.1 wt. % conversion of the decene-5 to respective aldehydes and alcohols.

To illustrate the reusability of the heterogeneous catalyst without an appreciable loss of activity, the recovered heterogeneous catalyst was washed with heptane to remove residual aldehyde and again charged to the autoclave along with 143 mmoles of decene-5. After conducting the hydroformylation reaction under an applied pressure of 240 atmospheres of carbon monoxide and hydrogen at a temperature of 160° C. for a period of 18 hours, the autoclave was cooled and the excess pressure was vented. The products were removed from the autoclave, the heterogeneous catalyst was separated from the liquid by decantation and the organic product was analyzed again by means of gas-liquid chromatography. The analysis disclosed that 84.1 wt. % of the decene-5 has been converted to aldehydes and alcohols. In addition, the liquids were found to contain only traces of dicobalt octacarbonyl, thus indicating that only negligible quantities of the cobalt were removed from the heterogeneous catalyst in subsequent operations as compared to the almost 42% loss of cobalt which occurred when the catalyst was first prepared. Therefore, the conclusion is reached by that utilizing a heterogeneous catalyst system in which a cobaltcontaining compound is chemically bonded to a zeolite-alumina sol dispersion, it is possible to reuse said catalyst in a series of experiments without appreciably affecting the activity of the catayst and its ability to convert olefinic hydrocarbons to aldehydes and alcohols when said olefinic compounds are treated with carbon monoxide and hydrogen.

EXAMPLE IV

In this example the physical parameters of Example II are maintained with the exception that faujasite is used as a substitute for the mordenite in the preparation of the catalystic composite as set forth in Example I. The amount of alcohol and aldehyde produced are seen to be greater than a reaction maintaining the physical parameters of Example II wherein the novel catalystic composite is not utilized.

EXAMPLE V

In this example the physical parameters of Examples II and III are maintained with the exception that stilbite is utilized in the place of the mordenite or faujasite. The hydroformylation reaction has a greater percentage of alcohol and aldehyde produced than would have normally been expected in a hydroformylation reaction wherein the novel catalytic composite had not been utilized.

I claim as my invention:

1. A process for the hydroformylation of an olefinic hydrocarbon which comprises treating said hydrocarbon with carbon monoxide and hydrogen at hydroformylation conditions in the presence of a catalyst system comprising a cobalt-containing compound chemically bonded to a zeolite-alumina hydrosol dispersion which has been aged at a temperature of from about 30° to about 500° C. and recovering the resultant hydroformylated products.

2. The process as set forth in claim 1 in which said hydroformulation conditions include a temperature of from about 75° to about 300° C. and pressue in the range of from about 1 to about 500 atmospheres.

3. The process as set forth in claim 1 in which said catalyst system contains from about 0.1 to about 20 wt. % of cobalt-containing compound and from about 99.1 to about 80 wt. % of zeolite-alumina hydrosol dispersion.

4. The process as set forth in claim 1 in which said cobalt-containing compound is hydridocobalt carbonyl.

5. The process as set forth in claim 1 in which said cobalt-containing compound is cobalt chloride.

6. The process as set forth in claim 1 in which said cobalt-containing compound is cobalt acetate.

7. The process as set forth in claim 1 in which said cobalt-containing compound is cobalt nitrate.

8. The process as set forth in claim 1 in which said zeolite-alumina hydrosol dispersion is aluminated mordenite.

9. The process as set forth in claim 1 in which said zeolite-alumina hydrosol dispersion is aluminated faujasite.

10. The process as set forth in claim 1 in which said zeolite-alumina hydrosol dispersion is aluminated stilbite.

11. The process as set forth in claim 1 in which said zeolite is treated with an alumina hydrosol.

12. The process as set forth in claim 11 in which said alumina hydrosol comprises 33% aluminum chloride and 67% aluminum sulfate.

13. The process as set forth in claim 1 in which said unsaturated compound is decene-5 and said hydroformylated product is 2-butyl-1-heptanol.

14. The process as set foth in claim 1 in which said unsaturated compound is butene-2 and said hydroformylated product is 2-methylbutanol.

15. The process as set forth in claim 1 in which said unsaturated compound is tetradecene-7 and said hydroformylated product is 2-hexyl-1-nonanol.

16. The process as set forth in claim 1 in which said unsaturated compound is hexadecene-1 and said hydroformylated product is 1-heptadecanol.

* * * * *